United States Patent

Inoue et al.

Patent Number: 5,439,994
Date of Patent: Aug. 8, 1995

[54] METHOD OF POLYMERIZING AN OLEFIN USING A NOVEL TRANSITION METAL COMPOUND

[75] Inventors: Norihide Inoue, Yokohama; Tetsunosuke Shiomura, Tokyo; Masahiro Kouno, Kanagawa; Yoshiho Sonobe; Kazumi Mizutani, both of Yokohama, all of Japan

[73] Assignee: Mitsui Toatsu Chemicals, Inc., Tokyo, Japan

[21] Appl. No.: 277,570

[22] Filed: Jul. 20, 1994

Related U.S. Application Data

[62] Division of Ser. No. 941,056, Oct. 8, 1992, Pat. No. 5,359,102.

[30] Foreign Application Priority Data

Mar. 11, 1991 [JP] Japan ............................ 3-44682

[51] Int. Cl.⁶ .................................................. C08F 4/642
[52] U.S. Cl. .................................... 526/114; 526/133; 526/160; 526/170; 526/127; 526/113; 526/114
[58] Field of Search ............... 526/114, 119, 127, 160, 526/170

[56] References Cited

U.S. PATENT DOCUMENTS

| | | | |
|---|---|---|---|
| 2,818,416 | 12/1957 | Brown et al. | 556/129 |
| 2,827,446 | 3/1958 | Breslow | 526/86 |
| 2,922,803 | 1/1960 | Kaufman | 556/53 |
| 2,952,670 | 9/1960 | Fischer | 526/160 |
| 3,046,288 | 7/1962 | Sloan et al. | 556/52 |
| 4,728,706 | 3/1988 | Farnham et al. | 526/172 |
| 4,892,851 | 1/1990 | Ewen et al. | 502/104 |
| 4,975,403 | 12/1990 | Ewen | 502/113 |

FOREIGN PATENT DOCUMENTS

| | | |
|---|---|---|
| 58-19309 | 2/1983 | Japan. |
| 60-35008 | 2/1985 | Japan. |
| 61-130314 | 6/1986 | Japan. |
| 64-66214 | 3/1989 | Japan. |
| 2-41303 | 2/1990 | Japan. |
| 2-274703 | 8/1990 | Japan. |
| 2-274704 | 11/1990 | Japan. |
| 3-179005 | 8/1991 | Japan. |
| 785760 | 11/1957 | United Kingdom. |
| 88/05792 | 8/1988 | WIPO. |
| 88/05793 | 8/1988 | WIPO. |

OTHER PUBLICATIONS

Brintzinger et al, J. Am. Chem. Soc., vol. 94, (1972) pp. 1219–1238.
Taube et al, J. of Organometallic Chem., vol. 347, (1988), pp. C9–C11.
Jordan et al, J. Am. Chem. Soc., vol. 109, (1987), pp. 4111–4113.
Zambelli et al, Macromolecules, vol. 22, (1989), pp. 2186–2189.

Primary Examiner—Mark Nagumo
Attorney, Agent, or Firm—Burns, Doane, Swecker & Mathis

[57] ABSTRACT

A novel transition metal compound represented by the formula

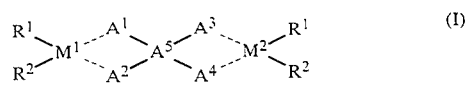

(wherein each of $A^1$, $A^2$, $A^3$ and $A^4$ is a cyclopentadienyl group, an indenyl group, a fluorenyl group or their derivative; $A^5$ is a hydrocarbondiylidene group having 4 to 30 carbon atoms; a pair of $A^1$ and $A^2$ as well as a pair of $A^3$ and $A^4$ is respectively bonded to the identical carbon atom in $A^5$ to form a crosslinking structure; each of $R^1$ and $R^2$ is a halogen atom, a hydrogen atom, an alkyl group or a silicon-containing alkyl group having 1 to 10 carbon atoms, an aryl group, an alkylaryl group, an arylalkyl group or a halogenated aryl group having 6 to 20 carbon atoms; $R^1$ and $R^2$ may be identical or different; each of $M^1$ and $M^2$ is titanium, zirconium or hafnium; and $M^1$ and $M^2$ may be mutually identical or different), and a method for polymerizing an olefin in the presence of this compound and a co-catalyst. The employment of the combination of the above-mentioned compound and another known transition metal compound as the transition metal compounds permits preparing a polyolefin having a wide molecular weight distribution.

6 Claims, 2 Drawing Sheets

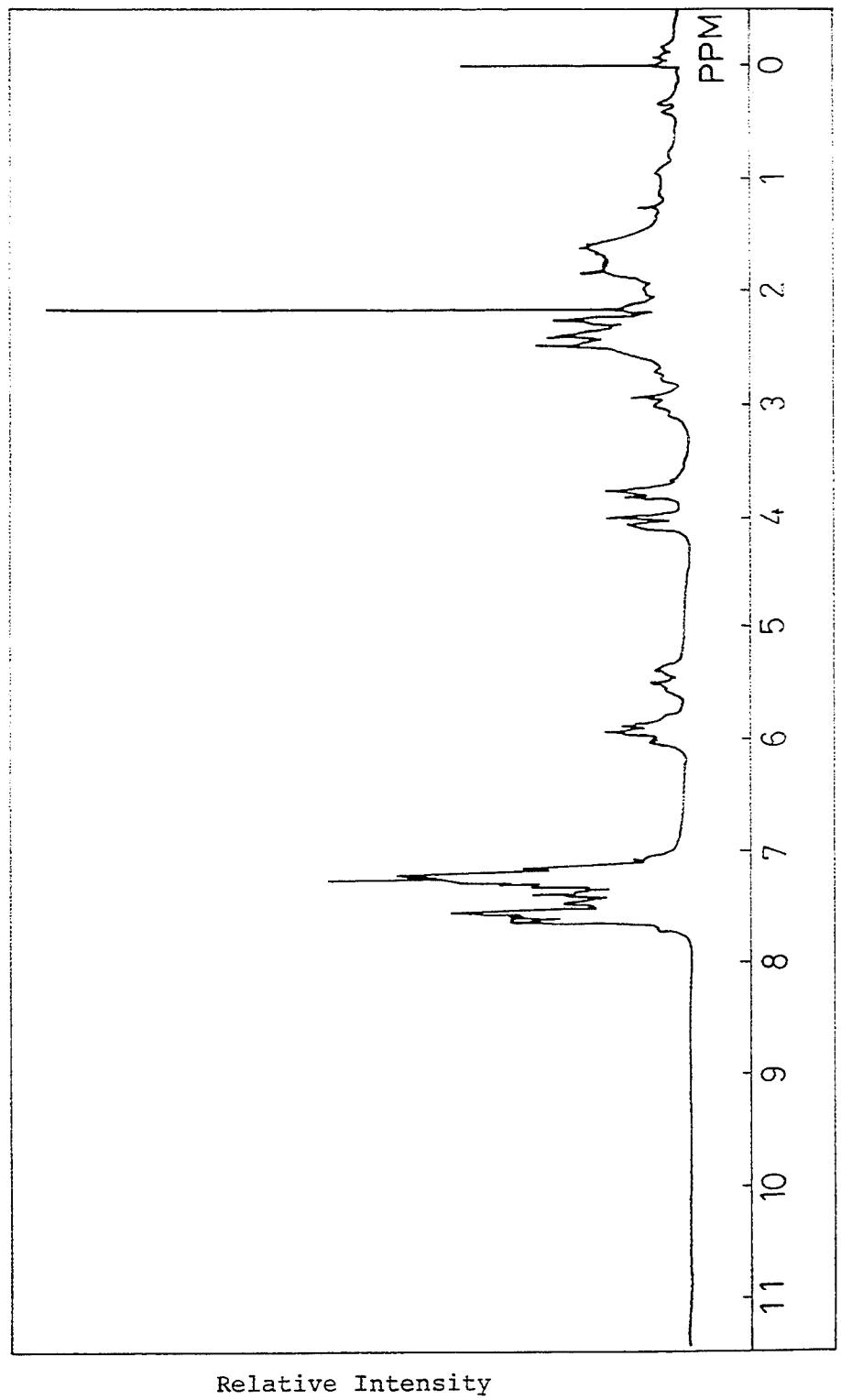

METHOD OF POLYMERIZING AN OLEFIN USING A NOVEL TRANSITION METAL COMPOUND

This application is a divisional, of application Ser. No. 07/941,056, filed Oct. 8, 1992, now U.S. Pat. No. 5,359,102.

BACKGROUND OF THE INVENTION

1. Field of the Invention

The present invention relates to a novel transition metal compound, and more specifically, it relates to a novel transition metal compound having two transition metal atoms in one molecule and a method for polymerizing an olefin by the use of the same.

2. Description of the Related Art

It is known that a transition metal compound having a cyclopentadienyl group, an indenyl group, a fluorenyl group or their derivative as a ligand, i.e., a so-called metallocene compound can be used together with a co-catalyst such as an aluminoxane to polymerize an olefin, whereby a polyolefin can be prepared.

Japanese Patent Application Laid-open Nos. 19309/'83 and 35008/'85 disclose a method for polymerizing or copolymerizing an olefin in the presence of a catalyst comprising a metallocene compound and an aluminoxane.

In Japanese Patent Application Laid-open Nos. 130314/'86 and 66214/'89, it is described that a catalyst comprising a metallocene compound having a bridged ligand and an aluminoxane can be employed to prepare a poly-α-olefin having a high isotactic degree.

In Japanese Patent Application Laid-open Nos. 41303/'90, 274703/'90 and 274704/'90, it is described that a catalyst comprising a metallocene compound having mutually asymmetric and bridged ligands and an aluminoxane can be used to prepare a syndiotactic poly-α-olefin.

On the other hand, some catalyst systems containing no aluminoxanes as the co-catalysts have been reported, since it was suggested that an active species of the above-mentioned catalyst, i.e., the so-called Kaminsky type catalyst is a transition metal cation which can be represented by $[Cp_2MR]^+$ (wherein Cp is a cyclopentadienyl derivative; M is Ti, Zr or Hf; and R is alkyl).

As described in J. Organometall. Chem. 347, C9 (1988), Taube et al. have succeeded in the polymerization of ethylene by the use of a compound represented by $[CP_2TiMe(THF)]^+[BPh_4]^-$ (wherein Me is a methyl group; Ph is a phenyl group, and THF is tetrahydrofuran).

Jordan et al. have suggested in J. Am. Chem. Soc., 109, 4111 (1987) that a zirconium complex represented by $[Cp_2ZrR(L)]^+$ (wherein R is a methyl group or a benzyl group; and L is a Lewis base) functions to polymerize ethylene.

In Japanese Patent Application Disclosure (Kohyo) Nos. 501950/'89 and 502036/'89, it is described that a catalyst comprising a cyclopentadienyl metal compound and an ionic compound capable of stabilizing cyclopentadienyl metal cation is used to polymerize an olefin.

Zambelli et al. have reported in Macromolecules, 22, 2186 (1989) that a catalyst comprising a combination of a zirconium compound containing a derivative of cyclopentadiene as a ligand, trimethyl aluminum and fluorodimethyl aluminum permits preparing an isotactic polypropylene.

Japanese Patent Application Laid-open No. 179005/'91 discloses an olefin polymerization catalyst comprising (a) a neutral metallocene compound, (b) an aluminum alkyl and (c) a Lewis acid.

In Japanese Patent Application Laid-open No. 41303/'90, there is described a method for preparing a polyolefin having a wide molecular weight distribution in the presence of a catalyst comprising two or more kinds of metallocene compounds and an aluminoxane, and in the catalyst for use in this method, a zirconium compound is mixed with a hafnium compound. In general, the hafnium compound has an extremely low polymerization activity, and therefore in order to effectively prepare the polyolefin having the wide molecular weight distribution, the polymerization is required to be carried out at a high temperature. In consequence, a problem such as the decline of steric regularity of the produced polymer has taken place sometimes.

Furthermore, in Japanese Patent Application Laid-open No. 35008/'85, it is described that a catalyst obtained by mixing two kinds of zirconium compounds having different structures is used to prepare polyethylene having a wide molecular weight distribution. However, such a known method using the zirconium compound is insufficient to effectively expand the molecular weight distribution.

SUMMARY OF THE INVENTION

The present inventors have intensively conducted research on a metallocene compound by which the above-mentioned problems can be solved and which permits effectively preparing a polyolefin having a wide molecular weight distribution by the use of a combination with a known metallocene compound. As a result, they have found that the employment of a novel transition metal compound having two transition metal atoms in one molecule can solve the above-mentioned problems, and the present invention has been completed on the basis of this knowledge.

Accordingly, one aspect of the present invention is directed to a novel transition metal compound represented by the formula

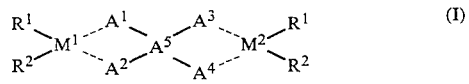 (I)

(wherein each of $A^1$, $A^2$, $A^3$ and $A^4$ is a cyclopentadienyl group, an indenyl group, a fluorenyl group or their derivative; $A^5$ is a hydrocarbondiylidene group having 4 to 30 carbon atoms; a pair of $A^1$ and $A^2$ as well as a pair of $A^3$ and $A^4$ is respectively bonded to the identical carbon atom in $A^5$ to form a crosslinking structure; each of $R^1$ and $R^2$ is a halogen atom, a hydrogen atom, an alkyl group or a silicon-containing alkyl group having 1 to 10 carbon atoms, an aryl group, an alkylaryl group, an arylalkyl group or a halogenated aryl group having 6 to 20 carbon atoms; $R^1$ and $R^2$ may be identical or different; each of $M^1$ and $M^2$ is titanium, zirconium or hafnium; and $M^1$ and $M^2$ may be identical or different).

Furthermore, the present invention is directed to a method for polymerizing an olefin by the use of a catalyst comprising the above-mentioned transition metal compound and a promoter, and a method for polymerizing an olefin which is characterized by polymerizing an olefin in the presence of a catalyst made from a promoter and at least two kinds of transition metal compounds comprising the above-mentioned transition metal compound and another transition metal compound represented by the formula

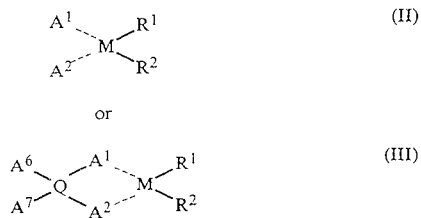

or $$A^6 \diagdown_Q \diagup^{A^1} \diagdown_{A^2} M \diagup^{R^1}_{R^2} \quad (III)$$

(wherein each of $A^1$ and $A^2$ is a cyclopentadienyl group, an indenyl group, a fluorenyl group or their derivative; $A^1$ and $A^2$ may be mutually identical or different; each of $A^6$ and $A^7$ is an alkyl group having 1 to 10 carbon atoms, an aryl group, an alkylaryl group, an arylalkyl group, a halogenated aryl group or a hetero-atom such as oxygen, nitrogen, sulfur or silicon atom-containing hydrocarbon group having 6 to 20 carbon atoms, or a hydrogen atom; Q is a hydrocarbon group or a silicon, germanium or tin-containing hydrocarbon group having 1 to 10 carbon atoms, which links with $A^1$ and $A^2$; $A^6$ and $A^7$ may be mutually bonded to form a ring structure composed of $A^6$, $A^7$ and Q; each of $R^1$ and $R^2$ is a halogen atom, a hydrogen atom, an alkyl group or a silicon-containing alkyl group having 1 to 10 carbon atoms, an aryl group, an alkylaryl group, an arylalkyl group or a halogenated aryl group having 6 to 20 carbon atoms; $R^1$ and $R^2$ may be mutually identical or different; and M is titanium, zirconium or hafnium).

The transition metal compound represented by the formula (I) is a novel compound, and when a syndiotactic polypropylene is prepared in accordance with the method of the present invention by the use of this novel transition metal compound, a high crystallization rate and a polymer having a low molecular weight can be effectively obtained. Furthermore, when this novel transition metal compound is used together with another known transition metal compound, a polyolefin having a wide molecular weight distribution can be prepared. Thus, it is fair to say that the novel transition metal compound is industrially very valuable.

BRIEF DESCRIPTION OF THE DRAWINGS

FIG. 2 shows the measured results of a $^1$H-NMR spectrum of 3,7-dicyclopentadienyl-3,7-difluorenyl-bicyclo-[3,3,0]octane obtained in Example 7.

DESCRIPTION OF THE PREFERRED EMBODIMENTS

Figure 1:
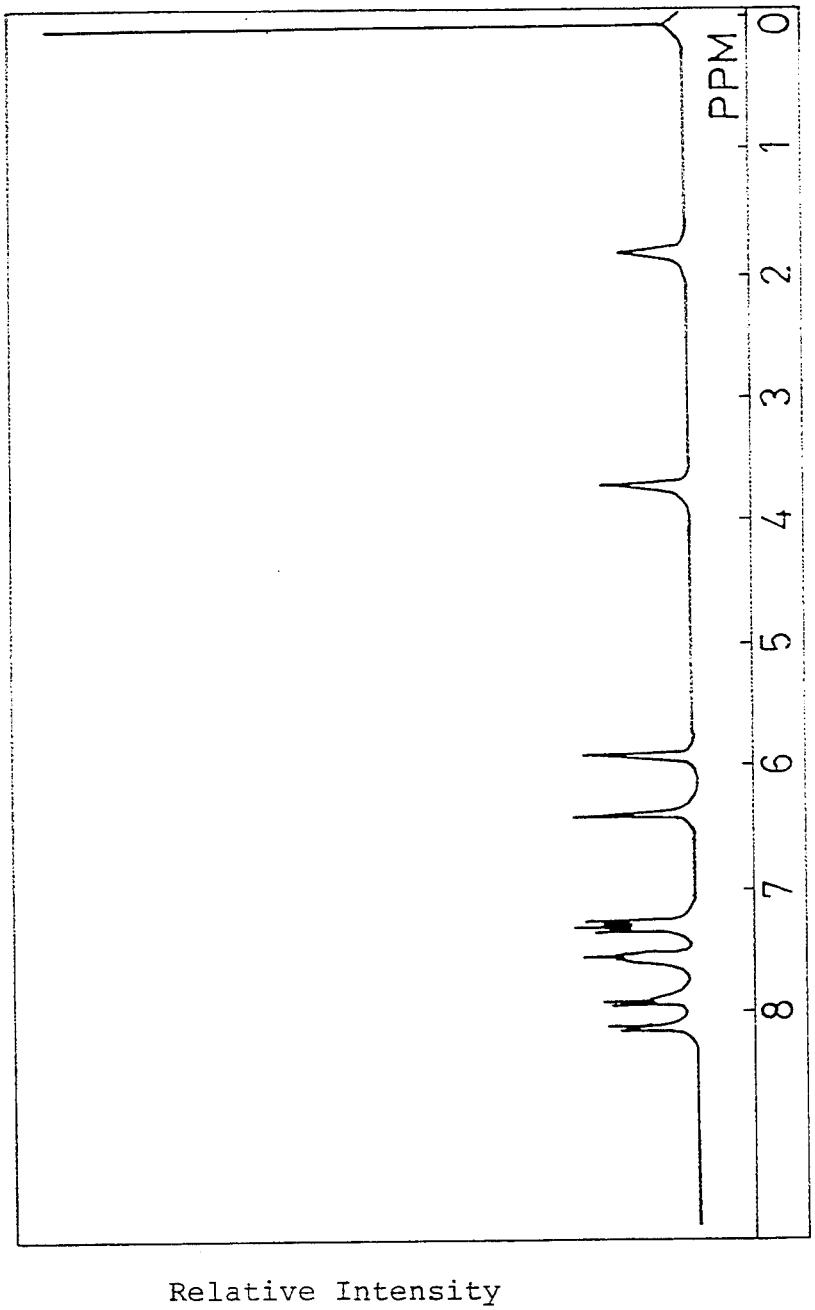
FIG. 1 shows the measured results of a hu 1H-NMR spectrum of 1,4-cyclohexanediylidenebis[(cyclopentadienyl-9-fluorenyl)zirconium dichloride obtained in Example 1.

A transition metal compound represented by the formula (I) which can be used in the present invention is a novel metallocene compound having two transition metal atoms in one molecule.

In the formula (I), each of $A^1$, $A^2$, $A^3$ and $A^4$ is a cyclopentadienyl group, indenyl group, fluorenyl group or their derivative. Typical examples of these groups include a cyclopentadienyl group, methylcyclopentadienyl group, dimethylcyclopentadienyl group, trimethylcyclopentadienyl group, tetramethylcyclopentadienyl group, indenyl group, 3-methylindenyl group, 4,5,6,7-tetrahydroindenyl group, fluorenyl group, 1-methylfluorenyl group and 2,7-di-t-butylfluorenyl group.

In the formula (I), $A^5$ is a hydrocarbondiylidene group having 4 to 30 carbon atoms. Typical examples of this group include a 2,3-butanediylidene group, 2,4-pentanediylidene group, 1,3-cyclopentanediylidene group, 4-cyclopentene-1,3-diylidene group, 2,5-hexanediylidene group, 1,4-cyclohexanediylidene group, 6-methyl-2,4-heptanediylidene group, bicyclo[3,3,0]octane-3,7-diylidene group, bicyclo[3,3,1]nonane-3,7-diylidene group and 9,10-anthracenediylidene group.

In the formula (I), each of $R^1$ and $R^2$ is a halogen atom, hydrogen atom, alkyl group or silicon-containing alkyl group having 1 to 10 carbon atoms, an aryl group, alkylaryl group, arylalkyl group or halogenated aryl group having 6 to 20 carbon atoms, and preferable examples are a methyl group and chlorine atom. M is titanium, zirconium or hafnium, and preferably it is zirconium or hafnium.

Typical examples of the transition metal compound having the formula (I) of the present invention include 2,5-hexanediylidenebis(dicyclopentadienylzirconium dichloride), 2,5-hexanediylidenebis[(cyclopentadienyl)(3-methylcyclopentadienyl)zirconium dichloride], 2,5-hexanediylidenebis[(cyclopentadienyl)(1-indenyl)zirconium dichloride], 2,5-hexanediylidenebis[(cyclopentadienyl)(9-fluorenyl)zirconium dichloride], 2,5-hexanediylidenebis[bis(methylcyclopentadienyl)zirconium dichloride], 2,5-hexanediylidenebis[(methylcyclopentadienyl)(1-indenyl)zirconium dichloride], 2,5-hexanediylidenebis[(methylcyclopentadienyl)(9-fluorenyl)zirconium dichloride], 2,5-hexanediylidenebis[(cyclopentadienyl)(2,7-di-t-butyl-9-fluorenyl)zirconium dichloride], 1,4-cyclohexanediylidenebis(dicyclopentadienylzirconium dichloride), 1,4-cyclohexanediylidenebis[(cyclopentadienyl)(3-methylcyclopentadienyl)zirconium dichloride], 1,4-cyclohexanediylidenebis[(cyclopentadienyl)(1-indenyl)zirconium dichloride], 1,4-cyclohexanediylidenebis[(cyclopentadienyl)(9-fluorenyl)zirconium dichloride], 1,4-cyclohexanediylidenebis[bis(methylcyclopentadienyl)zirconium dichloride], 1,4-cyclohexanediylidenebis[(methylcyclopentadienyl)(1-indenyl)zirconium dichloride], 1,4-cyclohexanediylidenebis[(methylcyclopentadienyl)(9-fluorenyl)zirconium dichloride], 1,4-cyclohexanediylidenebis[(cyclopentadienyl)(2,7-di-t-butyl-9-fluorenyl)zirconium dichloride], bicyclo[3,3,0]octane-3,7-diylidenebis(dicyclopentadienylzirconium dichloride), bicyclo[3,3,0]-octane-3,7-diylidenebis[(cyclopentadienyl)(3-methylcyclopentadienyl)zirconium dichloride], bicyclo[3,3,0]octane-3,7-diylidenebis[(cyclopentadienyl)(1-indenyl)zirconium dichloride], bicyclo[3,3,-0]octane-3,7-diylidenebis[(cyclopentadienyl)(9-fluorenyl)zirconium dichloride], bicyclo[3,3,0]-octane-3,7-diylidenebis[bis(methylcyclopentadienyl)zirconium dichloride], bicyclo[3,3,0]octane-3,7-diylidenebis[(methylcyclopentadienyl)(1-indenyl)zirconium dichloride], bicyclo[3,3,0]octane-3,7-diylidenebis[(methylcyclopentadienyl)(9-fluorenyl)zirconium dichloride], bicyclo[3,3,0]-octane-3,7-diylidenebis[(cyclopentadienyl)(2,7-di-t-butyl-9-fluorenyl)zirconium dichloride], bicyclo[3,3,1]nonane-3,7-diylidenebis(dicyclopentadienylzirconium dichloride), bicyclo[3,3,1]nonane-3,7-diylidenebis[(cyclopentadienyl)(3-methylcyclopentadienyl)zirconium dichloride], bicyclo[3,3,1]nonane-3,7-diylidenebis[(cyclopentadienyl)(1-indenyl)zirconium dichloride], bicyclo[3,3,1]nonane-3,7-diylidenebis[(cyclopentadienyl)(9-fluorenyl)zirconium dichloride], bicyclo[3,3,1]nonane-3,7-diylidenebis[(bis(-methylcyclopentadienyl)zirconium dichloride], bicyclo[3,3,1]nonane-3,7diylidenebis[(methylcyclopentadienyl)(1-indenyl)zirconium dichloride], bicyclo[3,3,1]nonane-3,7-diylidenebis[(methylcyclopentadienyl)(9-fluorenyl)zirconium dichloride], bicyclo[3,3,1]nonane-3,7-diylidenebis[(cyclopentadienyl)(2,7-di-t-butyl-9-fluorenyl)zirconium dichloride], and those compounds in which the zirconium atom of each compound is replaced with a hafnium atom.

The compound of the formula (I) can be synthesized, for example, in accordance with the following synthetic route.

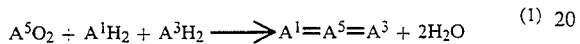  (1)

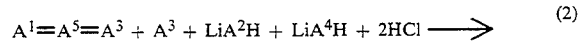  (2)

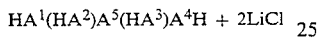

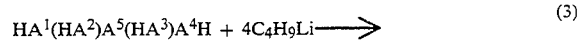  (3)

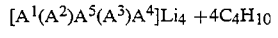

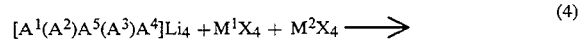  (4)

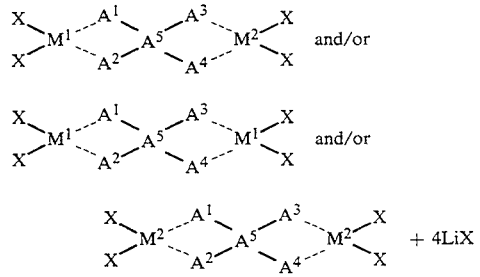

(wherein X is a halogen atom).

For example, in the case that the compound of the formula (I) is 1,4-cyclohexanediylidenebis[(cyclopentadienyl)(9-fluorenyl)zirconium dichloride] which will be referred to in undermentioned examples, the synthetic route is as follows.

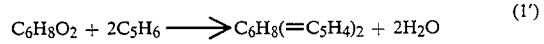  (1')

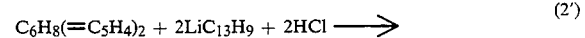  (2')

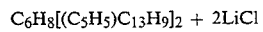

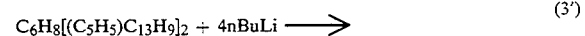  (3')

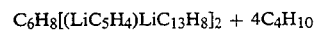

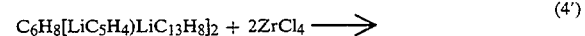  (4')

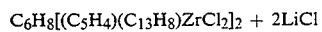

The halogen compound obtained by the above-mentioned formula (4) is reacted with an organometallic compound of a metal in the group IA or IIA of the periodic table such as $R^1Li$, $R^2Li$, $R^1MgCl$, or $R^2MgCl$ (each of $R^1$ and $R^2$ is an alkyl group or a silicon-containing alkyl group having 1 to 10 carbon atoms, an aryl group, an alkylaryl group, an arylalkyl group or a halogenated aryl group having 6 to 20 carbon atoms), thereby obtaining a compound in which at least one of X is replaced with $R^1$ or $R^2$.

The reaction of the formula (I) is carried out by reacting a diketone compound with cyclopentadiene or its derivative, indene or its derivative, fluorene or its derivative, or a mixture thereof in the presence of an amine in an alcohol. In this reaction, the synthetic method of a fulvene compound described in J. Org. Chem. 49, 1849 (1984) can be similarly employed.

Examples of the solvent which can be used in this reaction include alcohols such as methanol, ethanol and isopropanol, and ethers such as diethyl ether, tetrahydrofuran and 1,2-dimethoxyethane. Examples of the amine which can be used as a catalyst in this reaction include triethylamine, pyridine and pyrrolidine.

The reaction of the formula (2) is a reaction of the compound obtained by the formula (1) with an alkaline metal salt of cyclopentadiene or its derivative, indene or its derivative, fluorene or its derivative, or a mixture thereof. In the formula (2), a lithium salt is shown, but another alkaline metal salt may be acceptable.

The reaction of the formula (2) is known, and for example, it is described in Justus Liebig; Ann Chem., 511, 101 (1934); J. Organometal. Chem., 303, 213 (1986), J. Am. Chem. Soc., 112, 2030 (1990) and Japanese Patent Application Laid-open No. 41303/'90. In accordance with the described procedure, the reaction of the formula (2) can be carried out.

Examples of the solvent which can be used in the reaction of the formula (2) include ethers such as diethyl ether, tetrahydrofuran and 1,2-dimethoxyethane.

The compound obtained by the formula (2) can be reacted with an alkyl lithium in accordance with the formula (3) to form a tetralithium salt. The alkyl lithium may be replaced with an alkyl potassium or alkyl sodium to form a tetrapotassium salt or tetrasodium salt, and this product can be used in the subsequent reaction. Moreover, an organic metallic compound of a metal in the groups IA or IIA of the periodic table such as metallic lithium, metallic potassium, metallic sodium or magnesium can substituted for the above-mentioned organic alkaline metals.

Examples of the solvent which can be used in the reaction of the formula (3) include ethers such as diethyl ether, tetrahydrofuran and 1,2-dimethoxyethane, and saturated hydrocarbon compounds such as heptane, hexane and pentane.

In the reaction of the formula (3), a molar ratio of the alkaline metal or organic alkaline metal compound to $HA^1(HA^2)A^5(HA^3)A^4H$ is in the range of from 3.0 to 10.0, preferably from 4.0 to 8.0, and reaction temperature is in the range of from $-100°$ C. to $150°$ C., preferably from $-80°$ C. to $80°$ C.

Examples of the solvent which can be used in the reaction of the formula (4) include halogenated hydrocarbon compounds such as chloroform and methylene chloride, saturated hydrocarbon compounds such as heptane, hexane and pentane, aromatic hydrocarbon compounds such as benzene, toluene and xylene, and ethers such as diethyl ether, tetrahydrofuran and 1,2-dimethoxyethane.

In this reaction, a molar ratio of [A¹(A²)A⁵(A³)A⁴]-Li₄ to (M¹X₄+M²X₄) is in the range of from 0.4 to 3.0, preferably from 0.5 to 1.0, and reaction temperature is in the range of from −100° C. to 100° C., preferably from −90° C. to 50° C.

Furthermore, as described above, the compound obtained by the formula (4) can be reacted with a metallic organic compound such as R¹Li, R²Li, R¹MgCl or R²MgCl, whereby the halogen can be replaced with R¹ or R².

Examples of the solvent which can be used in this case include saturated hydrocarbon compounds such as heptane, hexane and pentane, aromatic hydrocarbon compounds such as benzene, toluene and xylene, and ethers such as diethyl ether, tetrahydrofuran and 1,2-dimethoxyethane. Furthermore, a molar ratio of the alkyl metallic compound to [X₂M¹A¹(A²)]A⁵[A³(A⁴)M²X₂] is in the range of from 1.0 to 10.0, preferably from 2.0 to 6.0, and reaction temperature is in the range of from −100° C. to 100° C., preferably from −90° C. to 80° C.

The formed compound of the formula (I) can be purified by recrystallization or sublimation.

The transition metal compound represented by the formula (I) can be used in combination with the undermentioned co-catalyst to polymerize an olefin, but in this case, when the compound represented by the formula (I) is used together with a known transition metal compound represented by the formula (II) or (III) as the transition metal compound, a polyolefin having a wide molecular weight distribution can be effectively prepared. Typical examples of such a known transition metal compound having a non-bridged ligand of the formula (II) include bis(cyclopentadienyl)zirconium dichloride, bis(pentamethylcyclopentadienyl)zirconium dichloride, (cyclopentadienyl)(pentamethylcyclopentadienyl)zirconium dichloride, and those compounds in which the zirconium atom of each compound is replaced with a hafnium atom.

Examples of the transition metal compound having the bridged ligand of the formula (III) include ethylenebis(1-indenyl)zirconium dichloride, ethylenebis(4,5,6,7-tetrahydro-1-indenyl)zirconium dichloride, dimethylsilylenebis(methylcyclopentadienyl)zirconium dichloride, dimethylsilylenebis(dimethylcyclopentadienyl)zirconium dichloride, isopropylidene(cyclopentadienyl)(9-fluorenyl)zirconium dichloride, isopropylidene(cyclopentadienyl)(2,7-di-t-butyl-9-fluorenyl)zirconium dichloride, diphenylmethylene(cyclopentadienyl)(9-fluorenyl)zirconium dichloride, those compounds in which the zirconium atom of each compound is replaced with a hafnium atom, and transition metal compounds mentioned in Japanese Patent Application Laid-open Nos. 9913/'91, 131488/'90, 21607/'91 and 106907/'91.

As the co-catalyst which can be used together with the transition metal compound at the time of the polymerization, there can be mentioned a co-catalyst comprising (a) an organic aluminum compound and (b) a compound capable of stabilizing transition metal cations, in addition to known aluminoxanes.

The aluminoxanes are compounds represented by the formula

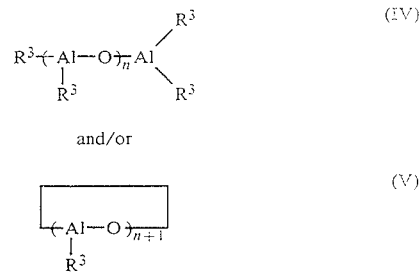

and/or

(wherein R³ is a hydrocarbon group having 1 to 10 carbon atoms, and n is an integer of 2 or more). In particular, a methylaluminoxane can be utilized in which R³ is a methyl group and n is 5 or more, preferably 10 or more. The contamination of the above-mentioned aluminoxane with a small amount of an alkylaluminum compound is allowable. In addition, there can be suitably utilized the aluminoxanes each having two or more kinds of alkyl groups mentioned in Japanese Patent Application Laid-open Nos. 24701/'90 and 103407/'91, the aluminoxanes in the state of fine particles mentioned in Japanese Patent Application Laid-open No. 198691/'88 and the like, and aluminum oxy compounds mentioned in Japanese Patent Application Laid-open Nos. 167302/'90 and 167305/'90, which are obtained by bringing the alumininoxanes into contact with water or an activated hydrogen compound.

In the polymerization method of the present invention, the molar ratio of the aluminoxane to the transition metal compound is in the range of from 1 to 100000, usually from 10 to 10000.

In the promoter comprising (a) the organic aluminum compound and (b) the compound capable of stabilizing transition metal cations, the organic aluminum compound which can be used as the component (a) can be represented by the formula $$R^4{}_jAl(OR^5)_kH_lX_m \qquad (VI)$$

(wherein each of R⁴ and R⁵ is a hydrocarbon group having 1 to 20 carbon atoms, and R⁴ and R⁵ may be mutually identical or different; X is a halogen atom; j is an integer of from 1 to 3; and each of k, l and m is an integer of from 0 to 2 and j+k+l+m=3).

Typical examples of the organic aluminum compound include trimethylaluminum, triethylaluminum, triisobutylalumimum, diethylaluminum chloride, ethylaluminum dichloride and diisobutylaluminum hydride. Above all, triethylaluminum and triisobutylalumimum can be suitably used.

As the compound capable of stabilizing the transition metal cations which can be used as the component (b), there can be mentioned an ionic compound containing an anion capable of stabilizing the transition metal cation and a cation which forms an ion pair with said anion, and a Lewis acidic compound.

Examples of the anions capable of stabilizing the transition metal cations include organic boron compound anions, organic arsenic compound anions, organic phosphorus compound anions, organic aluminum compound anions and organic gallium compound anions, and among others, what can be suitably utilized are the anions which have a relatively high bulk and which neither bond to nor strongly coordinate to a produced transition metal cation compound so as to keep up the activation of the polymerization-activating species. Examples of such suitable anions include tetraphenyl boron anions suggested by the above-mentioned Taube and Jordan, tetrakis(pentafluorophenyl)-boron anions mentioned in Japanese Patent Application Disclosure (Kohyo) Nos. 501950/'89 and 502036/'89 and Japanese Patent Application Laid-open No. 179006/'91, and aluminum compound anions and gallium compound anions formed by replacing boron atoms of these anions with aluminum atoms and gallium atoms, respectively.

No particular restriction is put on the cation for forming an ionic compound in the state of the pair with the anion, so long as it does not inactivate the polymerization-activating species. Examples of the cation include known cations capable of forming the pair with the above-mentioned anion. Examples of such cations include metallic cations, organometallic cations, carbonium cations, tripium cations and ammonium cations. Typical examples of the cations include silver cations, dicyclopentadienyl iron cations, triphenyl carbenium cations, triphenyl phosphonium cations, and tributylammonium cations.

The Lewis acidic compound may be a known compound showing Lewis acidity, and a compound which does not inactivate the polymerization-active species is acceptable without any particular limitation. The preferable example of the Lewis acidic compound is tris(-pentafluorophenyl)boron mentioned in Japanese Patent Application Laid-open No. 179005/'91.

The transition metal catalyst component and/or the promoter component in the polymerization of the present invention can be used without an additional treatment, but it may be supported on a carrier known as for a Ziegler catalyst, such as $SiO_2$, $Al_2O_3$ or $MgCl_2$.

No particular restriction is put on a polymerization process and polymerization conditions in the present invention, and there can be used a known method for the polymerization of α-olefin, a solvent polymerization method in which an inactive hydrocarbon solvent is employed, a mass polymerization method in which an inactive hydrocarbon medium is not substantially present, and a gaseous phase polymerization method. Polymerization temperature is in the range of from $-100°$ to $200°$ C., and polymerization pressure is usually in the range of from atmospheric pressure to 100 kg/cm$^2$-G. Preferably, the former is from $-50°$ to $100°$ C., and the latter is from atmospheric pressure to 50 kg/cm$^2$-G.

Examples of the hydrocarbon medium which can be used in the treatment of the catalyst component or the polymerization in the present invention include saturated hydrocarbons such as butane, pentane, hexane, heptane, octane, nonane, decane, cyclopentane and cyclohexane; and aromatic hydrocarbons such as benzene, toluene and xylene.

Examples of the olefin which can be used in the polymerization include olefins having 2 to 25 carbon atoms such as ethylene, propylene, 1-butene, 4-methyl-1-pentene, 1-hexene, 1-octene, 1-decene, 1-dodecene, 1-tetradecene, 1-hexadecene and 1-octadecene.

The present invention can be utilized not only in the homopolymerization of the olefin but also in the preparation of a copolymer of propylene and ethylene as well as a copolymer of propylene and another olefin having 2 to about 25 carbon atoms such as 1-butene.

Now, the present invention will be described in detail in reference to examples.

Example 1

Synthesis of transition metal compound

[1,4-biscyclopentadienylidenecyclohexane]

In a 500-cm$^3$ four-necked flask in which the atmosphere was replaced with nitrogen, 15 g of 1,4-cyclohexanedione and 36 g of cyclopentadiene were dissolved in 200 cm$^3$ of methanol. 34 cm$^3$ of pyrrolidine were added dropwise to the solution at 0° C. over 30 minutes, and the produced solid was collected by filtration and then washed with methanol, followed by drying, to obtain 39 g of brown 1,4-biscyclopentadienylidenecyclohexane.

[1,4-dicyclopentadienyl-1,4-difluorenylcyclohexane]

In a 500-cm$^3$ four-necked flask in which the atmosphere was replaced with nitrogen, 16.6 g of fluorene were dissolved in 150 cm$^3$ of tetrahydrofuran, followed by treating the solution with methyllithium, thereby obtaining a tetrahydrofuran solution of fluorenyllithium. Next, 200 cm$^3$ of a tetrahydrofuran solution containing 10.4 g of previously synthesized 1,4-biscyclopentadienylidenecyclohexane were added dropwise to the tetrahydrofuran solution at $-10°$ C. over 30 minutes. After completion of the addition, the reaction temperature was elevated up to room temperature, followed by stirring for 15 hours. Then, 200 cm$^3$ of a 3.6% hydrochloric acid solution were poured thereinto to bring the reaction to an end. The resultant solid was collected by filtration, washed with ether, and then dried to obtain 18.5 g of white powdery 1,4-dicyclopentadienyl-1,4-difluorenylcyclohexane.

[1,4-cyclohexanediylidenebis{(cyclopentadienyl)(9-fluorenyl)zirconium dichloride}]

Previously synthesized 1,4-dicyclopentadienyl-1,4-difluorenylcyclohexane was treated with n-butyllithium to prepare a tetralithium salt of 1,4-dicyclopentadienyl-1,4-difluorenylcyclohexane. Next, in a 500-cm$^3$ glass flask in which the atmosphere was replaced with nitrogen, 6.1 g of zirconium tetrachloride were suspended in 100 cm$^3$ of methylene chloride. 300 cm$^3$ of a methylene chloride solution in which 0.013 mol of the tetralithium salt of 1,4-dicyclopentadienyl-1,4-difluorenylcyclohexane was dissolved at $-78°$ C. were then added to the resultant suspension. After stirring at $-78°$ C. for 4 hours, the solution was heated up to room temperature, and at this temperature, the reaction was further continued for 15 hours. A reddish brown solution containing a white precipitate of lithium chloride was filtered and then concentrated, followed by cooling at $-30°$ C. for 24 hours, thereby obtaining 3.1 g of orange 1,4-cyclohexanediylidenebis[(cyclopentadienyl)(9 -fluorenyl)zirconium dichloride].

The elemental analysis values of the product were as follows:

|  | C | H | Cl | Zr |
|---|---|---|---|---|
| Calcd. (wt %) | 58.1 | 3.78 | 16.7 | 20.4 |
| Found (wt %) | 58.6 | 3.72 | 16.5 | 21.2 |

In addition, the measured results of $^1$H-NMR spectrum are shown in FIG. 1.

Example 2

Polymerization

In a 2-dm² autoclave in which the atmosphere was sufficiently replaced with nitrogen were placed 3.0 mg of previously synthesized 1,4-cyclohexanediylidenebis[(cyclopentadienyl)(9-fluorenyl)zirconium dichloride], 0.4 g of methylaluminoxane (polymerization degree=17.7) purchased from Toso Aczo Co., Ltd. and 1 dm² of toluene. Next, propylene was added thereto, and polymerization was then carried out at 20° C. for 1 hour, while the pressure in the system was maintained at 3 kg/cm²-G.

After the polymerization, the resultant slurry was taken out, filtered and then dried to obtain 100 g of syndiotactic polypropylene powder.

The intrinsic viscosity (hereinafter abbreviated to [$\eta$]) of the powder measured in a tetralin solution at 135° C. was 0.6 dl/g, and the molecular weight distribution (Mw/Mn) of the powder measured by GPC (gel permeation chromatography) was 2.7. According to a $^{13}$C-NMR measurement, the syndiotactic pentad fraction (rrrr) of the powder calculated on the basis of a peak intensity attributable to a methyl group observed at about 20.2 ppm was 0.91.

Furthermore, the isothermal semicrystallization rate (t ½) of the obtained syndiotactic polypropylene was measured by melting the same at 230° C. and then cooling it to 110° C. in accordance with a differential scanning calorimetric measurement (DSC), and as a result, the rate was 1 minute and 22 seconds.

Comparative Example 1

Polymerization

Polymerization was carried out by the same procedure as in Example 2 except that 3.0 mg of isopropylidene(cyclopentadienyl)(9-fluorenyl)zirconium dichloride synthesized by a method described in Japanese Patent Application Laid-open No. 41303/'90 were used as a catalyst, to obtain 126.4 g of a syndiotactic polypropylene powder. With regard to this powder, [$\eta$] was 1.39 dl/g; Mw/Mn was 2.2; rrrr was 0.91; and t ½ was 3 minutes and 42 seconds.

Comparing these results with those of Example 2, it is apparent that the crystallization rate of the syndiotactic polypropylene obtained by using the catalyst component of the present invention is higher, and moldability is conveniently better.

Example 3

Polymerization

Polymerization was carried out by the same procedure as in Example 2 except that 2.0 mg of 1,4-cyclohexanediylidenebis[(cyclopentadienyl)(9-fluorenyl)zirconium dichloride] synthesized in Example 1 and 1.0 mg of isopropylidene(cyclopentadienyl)(9-fluorenyl)zirconium dichloride synthesized by a method described in Japanese Patent Application Laid-open No. 41303/'90 were used as catalysts and that 0.4 g of methylaluminoxane was used as a promoter, to obtain 84.3 g of a syndiotactic polypropylene powder. With regard to this powder, [$\eta$] was 0.96 dl/g; Mw/Mn was 6.2; and rrrr was 0.91.

Comparative Example 2

Polymerization

Polymerization was carried out by the same procedure as in Example 3 except that 1.0 mg of isopropylidene(cyclopentadienyl)(9-fluorenyl)zirconium dichloride and 3.0 mg of isopropylidene(cyclopentadienyl)(9-fluorenyl)zirconium hafnium dichloride synthesized by a method described in Japanese Patent Application Laid-open No. 41303/'90 were used as catalysts, to obtain 39.2 g of a syndiotactic polypropylene powder. With regard to this powder, [$\eta$] was 1.42 dl/g; Mw/Mn was 2.5; and rrrr was 0.89. The above-mentioned process of performing the polymerization at 20° C. by the use of the mixed catalysts of the known zirconium compound and hafnium compound could not provide the polyolefin having a wide molecular weight distribution.

Example 4

Polymerization

In a 5.0-dm² autoclave in which the atmosphere was sufficiently replaced with nitrogen were placed 7.2 mg of 1,4-cyclohexanediylidenebis[(cyclopentadienyl)(9-fluorenyl)zirconium dichloride] synthesized in Example 1 and 4.0 mg of diphenylmethylene(cyclopentadienyl)(9-fluorenyl)zirconium dichloride synthesized by the process described in Japanese Patent Application Laid-open No. 274703/'90 as catalysts, and 2.8 g of methylaluminoxane as a promoter. Furthermore, 3.0 dm² of liquid propylene were added thereto to carry out polymerization at 40° C. for 1 hour. Next, a small amount of methanol was added thereto so as to bring the polymerization to an end, and unreacted propylene was purged, followed by drying, to obtain 497.4 g of a syndiotactic polypropylene powder. With regard to this powder, [$\eta$] was 2.06 dl/g; Mw/Mn was 14.3; and rrrr was 0.90.

Example 5

Polymerization

Polymerization was carried out by the same procedure as in Example 4 except that 4.5 mg of 1,4-cyclohexanediylidenebis[(cyclopentadienyl)(9-fluorenyl)zirconium dichloride] synthesized in Example 1 and 5.5 mg of diphenylmethylene(cyclopentadienyl)(9-fluorenyl)zirconium dichloride synthesized by the process described in Japanese Patent Application Laid-open No. 274703/'90 were used as catalysts, and that 1.0 g of triethylaluminum and 0.2 g of triphenylcarbeniumtetrakis(pentafluorophenyl) borate were used as promoters, to obtain 452.6 g of a syndiotactic polypropylene powder. With regard to this powder, [$\eta$] was 3.10 dl/g; Mw/Mn was 11.2; and rrrr was 0.89.

Example 6

Polymerization

In a 2-dm² autoclave in which the atmosphere was sufficiently replaced with nitrogen were placed 5.0 mg of 1,4-cyclohexanediylidenebis[(cyclopentadienyl)(9-fluorenyl)zirconium dichloride] synthesized in Example 1, 0.5 mg of dicyclopentadienylzirconium dichloride, 0.5 g of methylaluminoxane and 1 dm³ of toluene. Next, ethylene was added thereto, and polymerization was then carried out at 20° C. for 1 hour, while the pressure in the system was maintained at 5 kg/cm²-G.

After the polymerization, the resultant slurry was taken out, filtered and then dried to obtain 91.7 g of a polyethylene powder.

With regard to this polyethylene powder, [η] was 1.86 dl/g and Mw/Mn was 6.3.

Example 7

Synthesis of transition metal compound

[3,7-biscyclopentadienylidenebicyclo[3,3,0]octane]

In a 300-cm³ four-necked flask in which the atmosphere was replaced with nitrogen, 4.9 g of bicyclo[3,3,-0]octane-3,7-dione and 12 g of cyclopentadiene were dissolved in 100 cm³ of methanol. 12 cm³ of pyrrolidine was added dropwise to the solution at 0° C. over 30 minutes, and the produced solid was collected by filtration, washed with methanol, and then dried to obtain 5.3 g of yellow 3,7-biscyclopentadienylidenebicyclo[3,3,0]octane. [3,7-dicyclopentadienyl-3,7-difluorenylbicyclo[3,3,0]octane]

In a 300-cm³ four-necked flask in which the atmosphere was replaced with nitrogen, 7.4 g of fluorene were dissolved in 100 cm³ of tetrahydrofuran, followed by treating the solution with methyllithium, thereby obtaining a tetrahydrofuran solution of fluorenyllithium. Next, 50 cm³ of a tetrahydrofuran solution containing 5.2 g of previously synthesized 3,7-biscyclopentadienylidenebicyclo[3,3,0]octane were added dropwise to the tetrahydrofuran solution at −10° C. over 30 minutes. After completion of the addition, the reaction temperature was elevated up to room temperature, followed by stirring for 15 hours. Then, 100 cm³ of a 3.6% hydrochloric acid solution were poured thereinto to bring the reaction to an end. The resultant solid was collected by filtration, washed with ether, and then dried to obtain 7.6 g of white powdery 3,7-dicyclopentadienyl-3,7-difluorenylbicyclo[3,3,0]octane.

The elemental analysis values of this compound were as follows:

|  | C | H |
|---|---|---|
| Calcd. (C₄₄H₃₈, wt %) | 93.24 | 6.76 |
| Found (wt %) | 92.71 | 6.90 |

In addition, the measured results of ¹H-NMR spectrum are shown in FIG. 2.

[bicyclo[3,3,0]octane-3,7-diylidenebis{(cyclopentadienyl)(9-fluorenyl)zirconium dichloride}]

5.0 g of previously synthesized 3,7-dicyclopentadienyl-3,7-difluorenylbicyclo[3,3,0]octane were treated with n-butyllithium to prepare a tetralithium salt of 3,7-dicyclopentadienyl-3,7-difluorenylbicyclo[3,3,0]octane. Next, in a 300-cm³ glass flask in which the atmosphere was replaced with nitrogen, 4.1 g of zirconium tetrachloride were suspended in 100 cm³ of methylene chloride. 100 cm³ of a methylene chloride solution in which the tetralithium salt was dissolved at −78° C. were then added to the resultant suspension. After stirring at −78° C. for 4 hours, the solution was heated up to room temperature, and at this temperature, the reaction was further continued for 15 hours. A reddish brown solution containing a white precipitate of lithium chloride was filtered, concentrated, and then cooled at −30° C. for 24 hours, thereby obtaining 1.2 g of orange bicyclo[3,3,0]octane-3,7-diylidenebis[(cyclopentadienyl)(9-fluorenyl)zirconium dichloride].

The elemental analysis values of the product were as follows:

|  | C | H | Cl | Zr |
|---|---|---|---|---|
| Calcd. (C₄₄H₃₄Zr₂Cl₄, wt %) | 59.58 | 3.86 | 15.99 | 20.57 |
| Found (wt %) | 58.86 | 3.89 | 16.22 | 20.14 |

Example 8

Polymerization

Polymerization was carried out by the same procedure as in Example 2 except that 2.0 mg of bicyclo[3,3,-0]octane-3,7-diylidenebis[(cyclopentadienyl)(9-fluorenyl)zirconium dichloride] synthesized in Example 7 were used as a catalyst and 0.3 g of methylaluminoxane were used as a promotor, to obtain 72.4 g of a syndiotactic polypropylene powder. With regard to this powder, [η] was 0.91 dl/g; Mw/Mn was 2.4; rrrr was 0.89, and t ½ was 1 minute and 48 seconds.

We claim:

1. A method for polymerizing an olefin in the presence of a catalyst comprising a transition metal compound represented by the formula

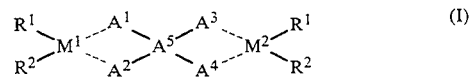

wherein each of $A^1$, $A^2$, $A^3$ and $A^4$ is a cyclopentadienyl group, an indenyl group, or a fluorenyl group; $A^5$ is a hydrocarbondiylidene having 4 to 30 carbon atoms; $A^1$ and $A^2$ are bonded to the identical carbon atom in $A^5$ and $A^3$ and $A^4$ are bonded to the identical carbon atom in $A^5$ to form a crosslinked structure; each of $R^1$ and $R^2$ is a halogen, hydrogen, alkyl having 1 to 10 carbon atoms or a silicon-containing alkyl having 1 to 10 carbon atoms, aryl having 6 to 20 carbon atoms, alkylaryl having 6 to 20 carbon atoms, arylalkyl having 6 to 20 carbon atoms or a halogenated aryl having 6 to 20 carbon atoms; $R^1$ and $R^2$ are identical or different; each of $M^1$ and $M^2$ is titanium, zirconium or hafnium; and $M^1$ and $M^2$ are mutually identical or different, and a promoter.

2. The method according to claim 1 wherein an aluminoxane is used as the co-catalyst.

3. The method according to claim 1 wherein (a) an organic aluminum compound and (b) a compound capable of stabilizing transition metal cations are used as the co-catalysts.

4. A method for polymerizing an olefin in the presence of a catalyst comprising a promoter and at least two kinds of transition metal compounds which comprise a combination of transition metal compound represented by the formula

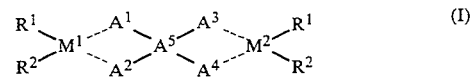

wherein each of $A^1$, $A^2$, $A^3$ and $A^4$ is a cyclopentadienyl group, an indenyl group, or a fluorenyl group; $A^5$ is a hydrocarbondiylidene having 4 to 30 carbon atoms; $A^1$ and $A^2$ are bonded to the identical carbon atom in $A^5$ and $A^3$ and $A^4$ are bonded to the identical carbon atom in $A^5$ to form a crosslinked structure; each of $R^1$ and $R^2$ is a halogen, hydrogen, alkyl having 1 to 10 carbon atoms or a silicon-containing alkyl having 1 to 10 carbon atoms, aryl having 6 to 20 carbon atoms, alkylaryl having 6 to 20 carbon atoms, arylalkyl having 6 to 20 carbon atoms, or a halogenated aryl having 6 to 20 carbon atoms; $R^1$ and $R^2$ are identical or different; each of $M^1$ and $M^2$ is titanium, zirconium or hafnium; and $M^1$ and $M^2$ are mutually identical or different, and another transition metal compound represented by the formula

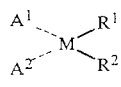 (II)

or

 (III)

wherein each of $A^1$ and $A^2$ is a cyclopentadienyl group, an indenyl group or a fluorenyl group; $A^1$ and $A^2$ are identical or different; each of $A^6$ and $A^7$ is an alkyl having 1 to 10 carbon atoms, aryl having 6 to 20 carbon atoms, alkylaryl having 6 to 20 carbon atoms, arylalkyl having 6 to 20 carbon atoms, halogenated aryl having 6 to 20 carbon atoms or a heteroatom-containing hydrocarbon group having 6 to 20 carbon atoms wherein the heteroatom is selected from the group consisting of oxygen, nitrogen, sulfur and silicon, or a hydrogen; Q is a hydrocarbon having 1 to 10 carbon atoms or a silicon, germanium or tin-containing hydrocarbon having 1 to 10 carbon atoms, which links with $A^1$ and $A^2$; $A^6$ and $A^7$ may be mutually bonded to form a ring structure composed of $A^6$, $A^7$ and Q; each of $R^1$ and $R^2$ is a halogen, hydrogen, alkyl having 1 to 10 carbon atoms or a silicon-containing alkyl having 1 to 10 carbon atoms, aryl having 6 to 20 carbon atoms, alkylaryl having 6 to 20 carbon atoms, arylalkyl having 6 to 20 carbon atoms or a halogenated aryl having 6 to 20 carbon atoms; $R^1$ and $R^2$ are identical or different; and M is titanium, zirconium or hafnium.

5. The method according to claim 4 wherein an aluminoxane is used as the co-catalyst.

6. The method according to claim 4 wherein (a) an organic aluminum compound and (b) a compound capable of stabilizing transition metal cations are used as the co-catalysts.

* * * * *